United States Patent
Szumanski

(10) Patent No.: US 10,987,057 B2
(45) Date of Patent: Apr. 27, 2021

(54) AVOIDING DRIVE CIRCUIT SATURATION IN AN ECG SYSTEM

(71) Applicant: Siemens Healthcare GmbH, Erlangen (DE)

(72) Inventor: Thomas Szumanski, McHenry, IL (US)

(73) Assignee: Siemens Healthcare GmbH, Erlangen (DE)

( * ) Notice: Subject to any disclaimer, the term of this patent is extended or adjusted under 35 U.S.C. 154(b) by 176 days.

(21) Appl. No.: 16/193,055

(22) Filed: Nov. 16, 2018

(65) Prior Publication Data

US 2020/0155072 A1 May 21, 2020

(51) Int. Cl.
*A61B 5/30* (2021.01)
*A61B 5/00* (2006.01)
*G05F 1/46* (2006.01)

(52) U.S. Cl.
CPC ............ *A61B 5/6843* (2013.01); *A61B 5/303* (2021.01); *A61B 5/7203* (2013.01); *A61B 2562/222* (2013.01); *G05F 1/46* (2013.01)

(58) Field of Classification Search
CPC .............................. A61B 5/0402; A61B 5/0428
See application file for complete search history.

(56) References Cited

U.S. PATENT DOCUMENTS

| | | | |
|---|---|---|---|
| 5,682,902 A | 11/1997 | Herleikson | |
| 2011/0295096 A1* | 12/2011 | Bibian | A61B 5/7203 600/372 |
| 2014/0194759 A1* | 7/2014 | Weiland | A61B 5/4806 600/509 |
| 2016/0367817 A1* | 12/2016 | Tol | A61N 1/0529 |
| 2018/0184980 A1* | 7/2018 | Qin | A61B 5/0205 |

OTHER PUBLICATIONS

D. K. Freeman, R. D. Gatzke, G. Mallas, Y. Chen and C. J. Brouse, "Saturation of the Right-Leg Drive Amplifier in Low-Voltage ECG Monitors," in IEEE Transactions on Biomedical Engineering, vol. 62, No. 1, pp. 323-330, Jan. 2015.

* cited by examiner

*Primary Examiner* — Allen Porter

(57) ABSTRACT

An Electrocardiography (ECG) system configured to produce an ECG output signal of a patient includes a plurality of electrodes, a monitoring circuit, a drive circuit, a lead circuit, and a control module. The electrodes form a plurality of leads. The monitoring circuit is configured to monitor a voltage differential on the leads and produce the ECG output signal. The drive circuit is configured to deliver a current to the electrodes based on a measured voltage at the electrodes. The lead fault detection system comprises one or more current sources configured to produce a current to deliver to the electrodes. The control module is configured to vary the current produced by the current sources based on a measured parameter at one or more of the electrodes.

18 Claims, 4 Drawing Sheets

AVOIDING DRIVE CIRCUIT SATURATION IN AN ECG SYSTEM

TECHNICAL FIELD

The present disclosure relates generally to methods, systems, and apparatuses related to avoiding drive circuit saturation in Electrocardiography (ECG) systems. The disclosed techniques are especially applicable to ECG systems that utilize low-voltage application specific integrated circuits (ASICs) or other low-voltage components.

BACKGROUND

Electrocardiography (ECG) systems are used to measure and monitor the cardiac function of a patient. Typically, electric potentials for measuring or deriving the heart signals are detected by an ECG system with ECG electrodes connected to a plurality of contact points or "leads" on the skin of the patient. These electrodes include measurement electrodes placed on the patient's chest that record the sum of the electrical activity of cardiac muscle fibers. This sum is referred to herein as the ECG output signal. In addition to the measuring electrodes, an additional electrode is placed on the patient's right leg used for potential compensation. This additional electrode, often referred to as "the right leg drive electrode" or the "RLD" electrode, provides a signal to a circuit (the "RLD circuit") that cancels noise and maintains common mode voltage across the ECG system. Typically, this circuit eliminates both the unwanted common mode alternating current (AC) and direct current (DC) signal content.

As with many electronic systems, the various electrical components of an ECG system have evolved a great deal in recent years. The components of ECG systems are becoming increasingly miniaturized. At the same time, lower voltage application specific integrated circuits (ASICs) specifically tailored for ECG systems have been designed with much lower voltage requirements than their predecessors. These low-voltage ECG ASICs are now the first (and some cases only) solution recommended by ECG component manufacturers.

Modern low-voltage ECG systems suffer from a particular drawback that will likely impede widespread market implementation and further miniaturization efforts until solved. In particular, the RLD circuit may be easily saturated by typical ECG electrode impedances. The traditional solution to this problem is to add a high performance hardware preamplifier circuit to the front end of the ASIC at a higher voltage. However, this solution is not desirable in modern ECG design due to its large size and higher voltage power infrastructure.

SUMMARY

Embodiments of the present invention address and overcome one or more of the above shortcomings and drawbacks, by providing methods, systems, and apparatuses related to avoiding saturation of the right leg drive circuit in ECG systems. Briefly, the charge of each individual electrode is balanced irrespective of the RLD circuitry by varying the amount of bias current flowing into each electrode via the current source sense signal. This technology described herein maximizes the removal of unwanted DC signal content from an ECG system on an electrode by electrode basis and paves the way for the next generation of ECG system miniaturization.

According to some embodiments, an ECG system configured to produce an ECG output signal of a patient includes a plurality of electrodes, a monitoring circuit, a drive circuit, a lead circuit, and a control module. The electrodes form a plurality of leads. The monitoring circuit is configured to monitor a voltage differential on the leads and produce the ECG output signal. The drive circuit is configured to deliver a current to the electrodes based on a measured voltage at the electrodes. The lead fault detection system comprises one or more current sources configured to produce a current to deliver to the electrodes. The control module is configured to vary the current produced by the current sources based on a measured parameter at one or more of the electrodes.

According to other embodiments, a method for avoiding oversaturation of a right leg drive circuit in an ECG system includes measuring one or more parameters associated with bias currents flowing from a plurality of electrodes connecting a patient to the right leg drive circuit. The method further includes determining, based on the measured parameters, an amount of current leakage in the ECG system due to a contact state of a first electrode included in the plurality of electrodes. Then, the bias current flowing into the first electrode is adjusted via a current source to compensate for the amount of current leakage.

According to other embodiments, an ECG system configured to produce an ECG output signal of a patient includes a plurality of electrodes, a monitoring circuit, a lead circuit, and a control module. The electrodes form a plurality of leads. The monitoring circuit is configured to monitor a voltage differential on the leads and produce the ECG output signal. The lead fault detection system includes one or more current sources configured to produce a current to deliver to the electrodes. The control module is configured to (a) apply a pulsed direct current to the current sources, (b) identify an expected signal based on a time-amplitude correlation of the pulsed direct current, and (c) remove an artifact from the ECG output signal that corresponds to the expected signal.

Additional features and advantages of the invention will be made apparent from the following detailed description of illustrative embodiments that proceeds with reference to the accompanying drawings.

BRIEF DESCRIPTION OF THE DRAWINGS

The foregoing and other aspects of the present invention are best understood from the following detailed description when read in connection with the accompanying drawings. For the purpose of illustrating the invention, there are shown in the drawings embodiments that are presently preferred, it being understood, however, that the invention is not limited to the specific instrumentalities disclosed. Included in the drawings are the following Figures.

DETAILED DESCRIPTION

Systems, methods, and apparatuses are described herein which relate generally to the addressing oversaturation in the RLD circuits of an ECG system by removing unwanted DC signal content on an electrode by electrode basis. As explained above, DC signal content is supplied through the RLD circuit as part of a lead fault detection function. However, variations in the electrodes (e.g., increased resistance due to a lack of solid contact) may result in an unexpected impedance that results in excess current build-up that may produce drive circuit saturation. Tuning each electrode as described herein eliminates unwanted DC charge injection from the RLD circuitry thereby allowing for the maximum utilization of the drive circuit in eliminating unwanted common mode AC content from the system and providing the best possible common mode rejection.

In a first example, a disclosed embodiment utilizes current source control to adjust the current supplied as part of the lead fault detection system to match resistance at the electrodes. For example, the lead fault detection circuit may adjust a current flowing into the drive circuit in order to balance a charge at each electrode. The lead fault detection circuit may balance the charge at each individual electrode irrespective of the drive circuit by varying the amount of current flowing into each electrode.

In some embodiments, the lead fault detection circuit may adjust the current flowing into the drive circuit on an electrode-by-electrode basis. For example, the lead fault detection circuit may measure a parameter at one or more of the plurality of electrodes. The lead fault detection circuit may use this parameter, such as a resistance at the electrode, to determine an amount of voltage that has "leaked" into the ECG system. This "leaked" voltage may otherwise build-up on the drive circuit. The lead fault detection circuit may measure a parameter indicative of this voltage and adjust the associated current source in order to compensate for it and avoid build-up of current on the drive circuit amplifier output of the ECG system.

In a second example, an embodiment uses a pulsed current in place of a steady DC input. The pulsed current may be injected into either the limb leads or the drive circuit. The pulsed current avoids the problem of continuous DC charge build-up on the drive circuit that may lead to saturation. The rest periods between each pulse allow the charge build-up to reset but can be set to be short enough such that lead fault detection is still possible.

Figure 1:
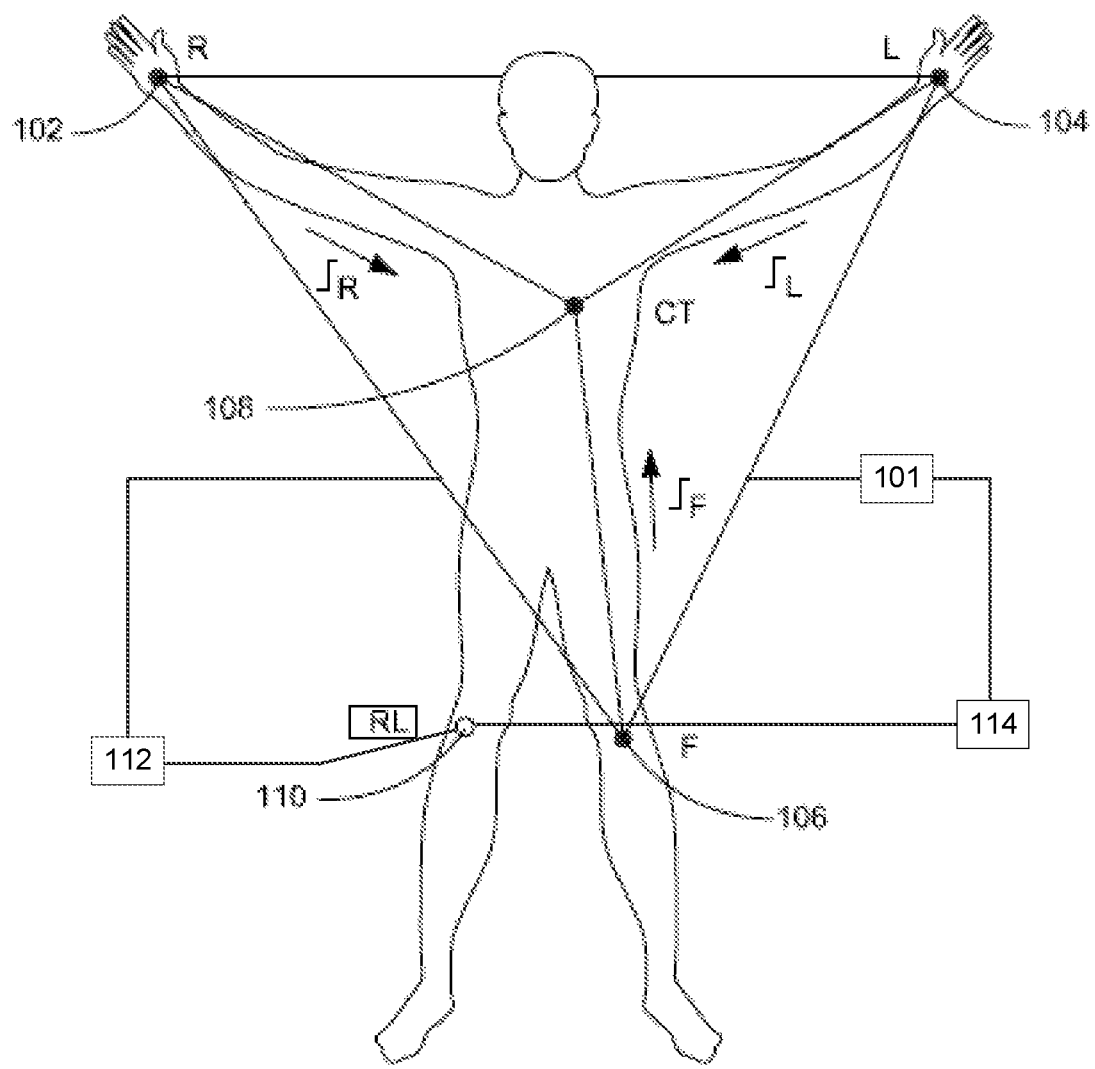
FIG. 1 is a diagram of an ECG system applied to a patient, according to some embodiments.

FIG. 1 is an example diagram of an ECG system 100. The ECG system 100 includes a monitoring circuit 101 connected to a first electrode 102, a second electrode 104, and a third electrode 106 positioned on a patient. In an exemplary embodiment, the first electrode 102 is a right arm electrode R, the second electrode 104 is a left arm electrode L, and the third electrode 106 is a leg (e.g., left leg) or foot electrode F. The three electrodes correspondingly create three limb leads L1, L2, and L3. The voltages at the three electrodes 102, 104, 106 are measured and used to determine a central terminal 108. The central terminal 108 (e.g., Wilson's central terminal) is an average of the voltages at the three electrodes 102, 104, 106 relative to a reference voltage (not shown in FIG. 1). The central terminal 108 may be used as a virtual electrode for additional leads, such as precordial leads, which are associated with separate chest electrodes. The monitoring circuit 101 monitors the voltage difference between the relevant leads to ultimately produce the ECG output signal.

The ECG system 100 further illustrates a fourth electrode 110. The fourth electrode 110, in an exemplary embodiment, is a right leg (RL) electrode. The fourth electrode 110 is an element of a drive circuit 112, such as a RLD circuit. One of the purposes of the drive circuit 112 is to remove noise from the ECG. There are at least two types of noise that are found at the drive circuit 112. A first type of noise is common mode noise. The drive circuit 112 is configured to cancel the common mode noise, a concept known in the art as common mode rejection. Effective common mode rejection allows the monitoring circuit 101 to more accurately detect the desired signals at the electrode locations, without interference from common mode noise. A second type of noise at the drive circuit 112 is DC noise that leaks to drive circuit 112 from a lead fault detection circuit 114. While the monitoring circuit 101, drive circuit 112, and lead fault detection circuit 114 are illustrated as separate components, it should be understood that the ECG system 100 may be made up of only one circuit with features that contribute to one or more of monitoring, noise cancellation, or lead fault detection.

Regarding common mode noise, the patient's body will often possess detectable signals that are present at each of the electrode locations and measured by each electrode. The drive circuit 112 cancels the common mode noise by using the voltage at the central terminal 108 (e.g., the average voltage at the first, second, and third electrodes 102, 104, 106), inverting the signal, and applying the inverted voltage signal to the fourth electrode 110.

The lead fault detection circuit 114 is a source of the second type of noise that is found at the drive circuit 112. The lead fault detection circuit 114 includes a current source for each lead that produces a DC current flow to each electrode of the ECG system 100. If an electrode loses contact with the body of the patient, the resistance at the electrode increases and is detected by the lead fault detection circuit 114. For instance, if the voltage at an electrode exceeds a threshold, an alert may be generated to indicate that an electrode is not properly positioned. If the DC current faces no resistance at the electrodes, then there will be minimal build-up of DC noise at the drive circuit 112. However, in practice, the electrodes provide some resistance, resulting in a build-up of current on the output of the drive circuit 112. As this current builds up the drive circuit 112 may saturate, degrading performance of the ECG system 100.

Figure 2:
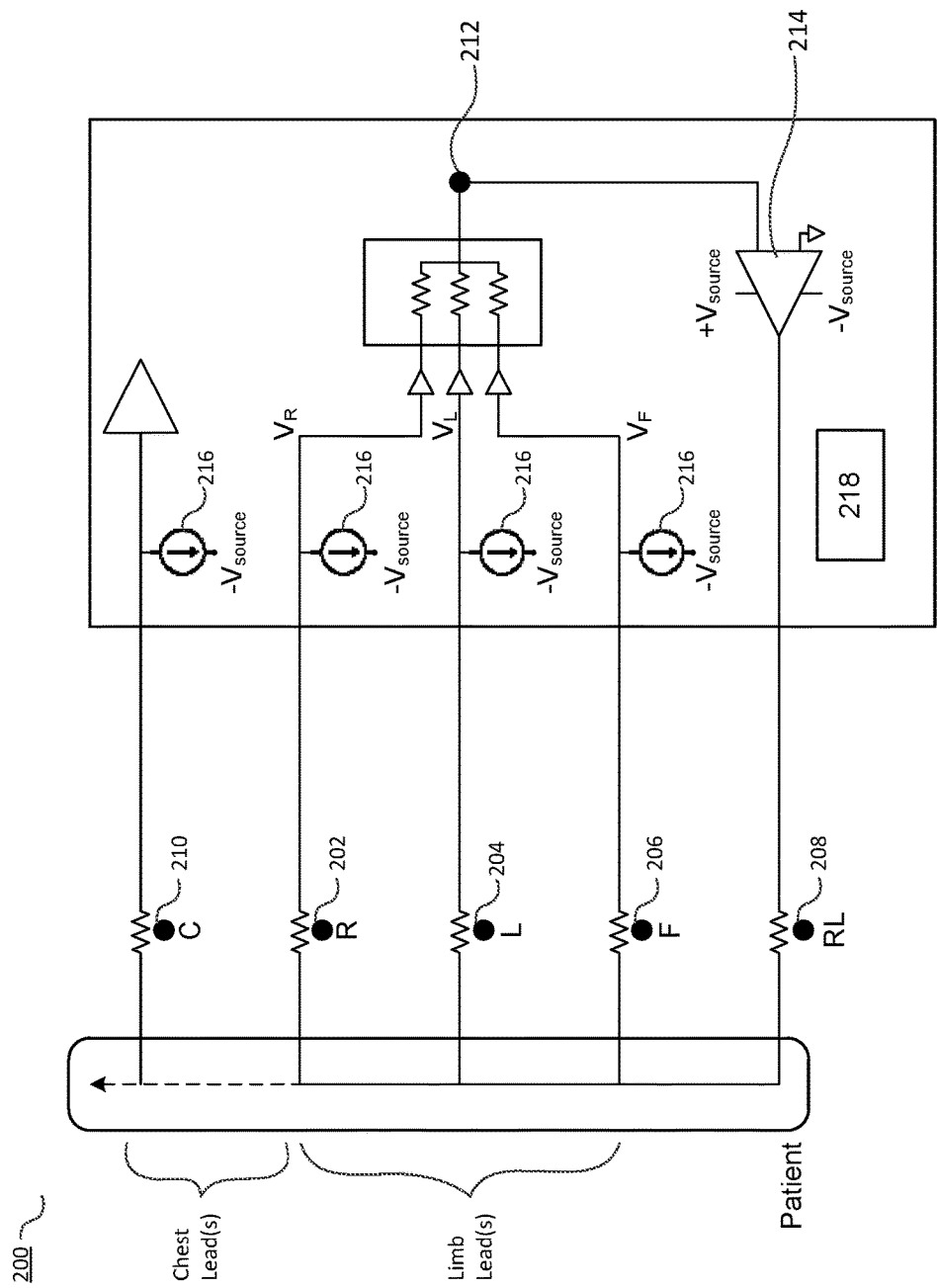
FIG. 2 is a circuit diagram of the ECG system and an associated drive circuit and lead fault detection circuit, according to some embodiments.

FIG. 2 is a circuit 200 that represents an embodiment of the ECG system 100. The circuit 200 includes a plurality of electrodes for forming a plurality of leads. For example, the circuit 200 may include a four-electrode, six-lead configuration, a ten-electrode, twelve-lead configuration, or other ECG configuration. In an exemplary embodiment, the circuit 200 includes at least a first electrode 202 (e.g., right arm electrode R), a second electrode 204 (e.g., left arm electrode L), and a third electrode 206 (e.g., left leg or foot electrode F). These electrodes together form limb leads that are used to produce an ECG output signal through monitoring of the voltage differences on the leads within a target frequency band in a manner known in the art. These voltage differences may be determined based on voltage measurements $V_R$, $V_L$, and $V_F$ taken at the electrodes 202, 204, and 206, respectively.

The circuit 200 further includes a fourth electrode 208 (e.g., a right leg electrode RL). The fourth electrode 208 may be an element of a drive circuit to cancel common mode AC noise. In some embodiments, the circuit 200 may be a four-electrode ECG system. In other embodiments, the circuit 200 may further include one or more chest electrodes 210 that create precordial leads as part of a 12-electrode ECG system, for example. It should be understood that the circuit 200 may include additional or alternative features to those illustrated. For example, additional electrodes may be employed in some embodiments.

The circuit 200 further includes a Wilson terminal 212 that is calculated as an average voltage of $V_R$, $V_L$, and $V_F$. The Wilson terminal 212 voltage is inverted and amplified by a drive circuit amplifier 214. The drive circuit amplifier 214 includes an output to the fourth electrode 208. The output of the drive circuit amplifier 214 offsets the common mode AC noise such that the circuit 200 is able to produce accurate ECG measurements in the target frequency band.

The circuit 200 further includes a plurality of current sources 216. Each current source 216 may be associated with a respective one of the first electrode 202, second electrode 204, third electrode 206, and one or more of the chest electrodes 210. The current sources 216 may be part of a lead fault detection feature of the circuit 200. The current sources 216 may deliver direct current to the plurality of electrodes. For example, each current source 216 may produce 100 mA that is directed to the associated electrode 202, 204, 206. The circuit 200 further includes a control module 218 that measures a resistance at each electrode 202, 204, 206. If any one of the electrodes 202, 204, 206 become dislodged or removed from the patient, an increased resistance will be detected by the control module 218. If the resistance exceeds a threshold value, the control module 218 produces an alert (e.g., an auditory alert or an alert displayed on a graphical user interface (GUI)). In this way, the circuit 200 includes a lead fault detection function.

As described above, there is the potential for additional DC build-up on the drive circuit amplifier 214 output due to the lead fault detection function and the current produced by the current sources 216. The individual currents that are associated with each current source 216 add up on the drive circuit amplifier 214 because all of these currents travel through the drive circuit and the fourth electrode 208 in order to create a complete circuit through each individual electrode 202, 204, 206. In other words, for a four-electrode configuration with each limb lead current source 216 producing 100 mA, 300 mA of direct current will be added to the output of the drive circuit amplifier 214. In greater electrode configurations, the DC content flowing through the drive circuit amplifier 214 will be even greater. With this direct current, there is the possibility of voltage "leaking" and causing build-up on the output of the drive circuit amplifier 214. For instance, if the impedance at one or more of the electrodes 202, 204, 206, 208, 210 is not what is expected (e.g., because of less-than-ideal contact between an electrode and the patient), then excess current may be present in the circuit 200. This DC build-up may cause saturation of the drive circuit amplifier 214 and thereby degrade the performance of the ECG system.

According to an exemplary embodiment, the control module 218 is configured to adjust the current sources 216 in order to compensate for excess current that is being supplied to the drive circuit amplifier 214 and causing an unwanted build-up of DC content that may lead to saturation of the drive circuit.

Figure 3:
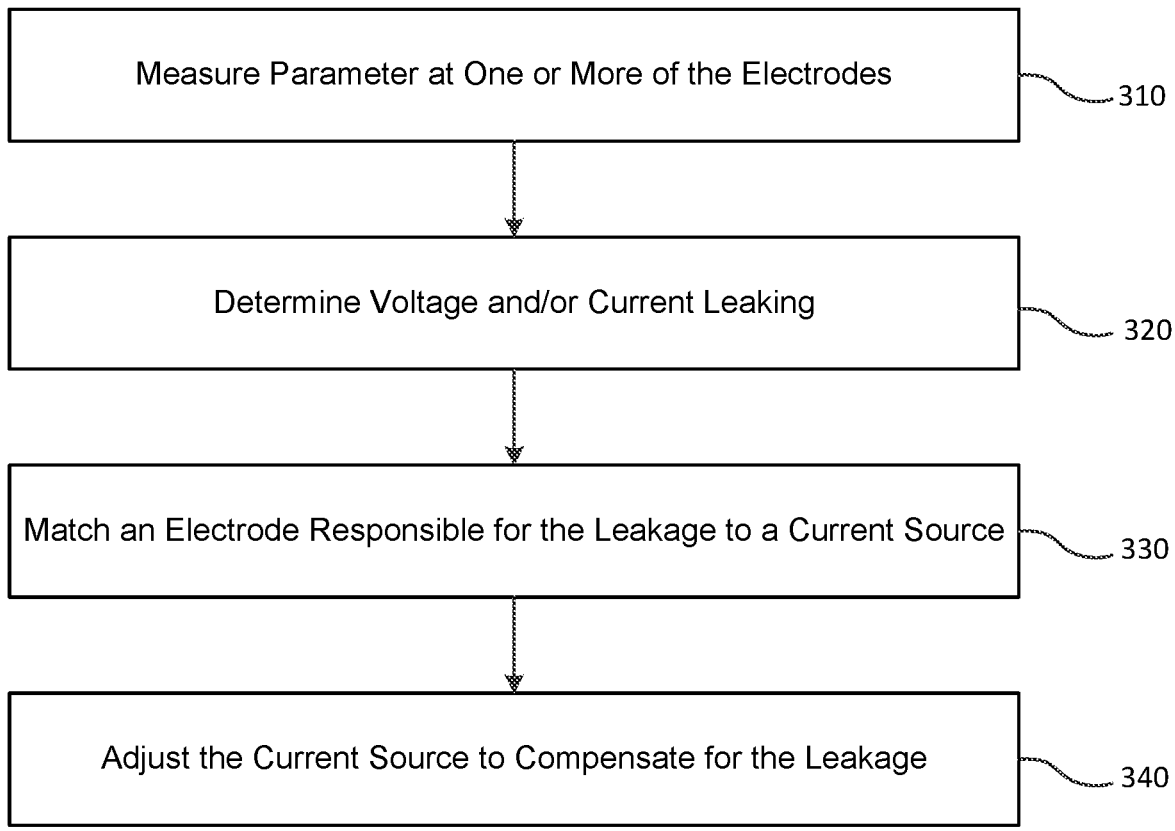
FIG. 3 is a flowchart of an exemplary process for varying a current source to avoid DC build-up on a drive circuit, according to some embodiments.

FIG. 3 is a flowchart of an exemplary process 300 for varying a current source 216 to avoid DC build-up on the drive circuit amplifier 214. In step 310, the control module 218 measures a parameter at one or more of the electrodes 202, 204, 206, 208, 210. For example, the control module 218 may measure resistance, impedance, voltage, and/or current at each electrode. In step 320, the control module 218 determines an amount of voltage and/or current leakage that is occurring at the associated electrode 202, 204, 206, 208, 210. In step 330, the control module 218 matches the leakage to one of the electrodes 202, 204, 206, 208, and 210 to identify the current source 216 associated with the electrode. In step 340, the control module 218 adjusts one or more of the current sources 216 in order to compensate for the mismatch on the circuit 200 due to the measured parameter. In one example, the control module 218 adjusts the current source 216 associated with the matched electrode determined at step 330. For instance, if the control module 218 determines that −20 mA of excess current is due the connection of the second electrode 204, the control module 218 may inject 20 mA into the circuit 200 via the current source 216 associated with the second electrode 204. If the control module 218 determines that the leakage is due to an increase resistance of the fourth electrode 208 (i.e., the RLD circuit electrode), the control module 218 may select a designated one of the current sources 216 and/or may adjust each of the current sources 216 to address the leakage.

As a result of the process 300, the control module 218 may discretely or periodically inject current into the circuit 200 through one or more of the current sources 216 in order to compensate for DC leakage that builds-up on the drive circuit amplifier 214. If the current injections are cyclical, the periodic injections may alias a signal that could produce an artifact that skews the actual ECG monitoring function. Therefore, in order for process 300 to be implemented, the rate of charge injection on each electrode 202, 204, 206, 208, 210 by the control module 218 should be below the minimum high pass filter setting of the monitoring function of the circuit 200. For instance, the rate of charge injections may be less than 0.05 Hz to avoid unwanted low frequency content from appearing in the actual measured ECG signal.

The present disclosure describes an ECG system that includes a control module 218 that is configured to compensate for current or voltage leaks that occur due to the DC content produced by a lead fault detection circuit within the ECG system. The control module 218 is configured to measure a parameter at each electrode and perform discrete and/or periodic current injections in order to balance the circuit and avoid direct current build-up on the drive circuit, which receives the sum of all of the current supplied by the current sources (due to the configuration of a drive circuit in ECG systems).

Figure 4:
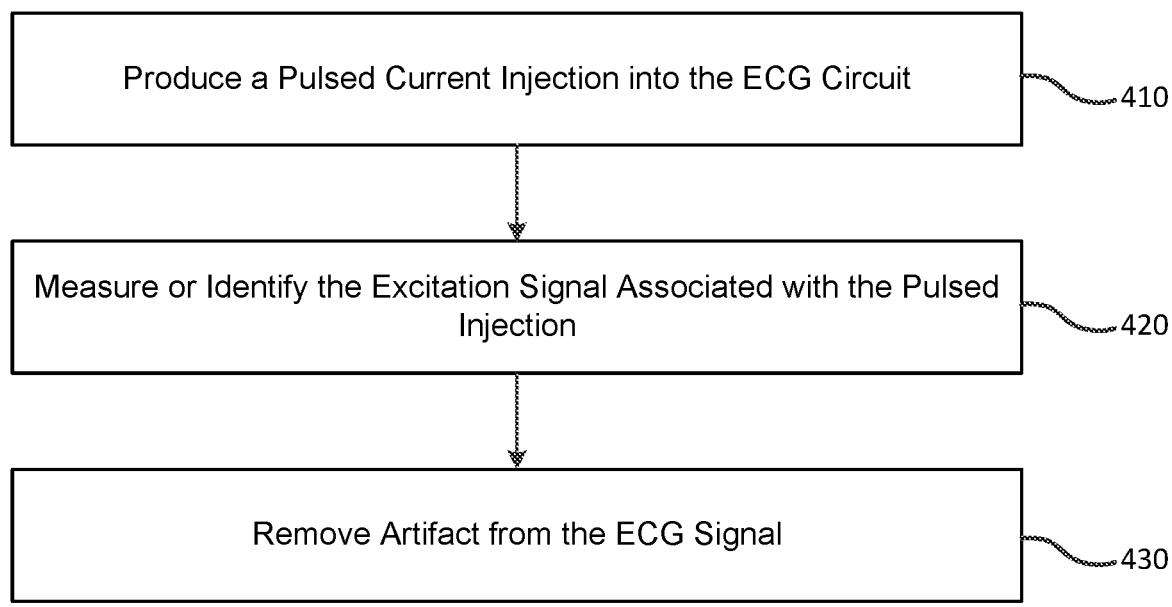
FIG. 4 is a flowchart of an exemplary process for applying a pulsed current in a lead fault detection system to avoid DC build-up on a drive circuit, according to some embodiments.

FIG. 4 is a flowchart of a process 400 for using a pulsed current as a supplement or alternative to the process 300 for addressing the problem of DC build-up on a drive circuit. In step 410, the control module 218 creates a feed of pulsed direct current from each current source 216, thereby creating a pulsed voltage at each electrode 202, 204, 206, 208, 210. Pulsed voltages and/or currents injected into either the leads or drive circuit help to avoid unwanted charge build-up on the circuit 200 (e.g., on the drive circuit amplifier 214). For example, the "rest" time created by the pulsed current allows the current to go to ground and avoids a current build-up on the drive circuit amplifier 214. This pulsed functionality thereby enhances the ability of the circuit 200 to avoid saturation of the drive circuit. However, the periodic nature of the pulsed current injections may alias frequency content that is then mistaken for a signal that is measured as the actual ECG output.

To address the aliasing, in step 420, the control module 218 measures or identifies the excitation signal associated with the pulsed direct current injections. For example, the control module 218 may perform a time-amplitude correlation to identify a signal that might be expected to be found as an artifact in an actual ECG signal due to the pulsing current. In step 430, the control module 218 removes the artifact from the ECG signal prior to it being output to a user.

The control module 218 may use any of a number of signal processing techniques that may be used to find a portion of a signal based on a known time-amplitude of the signal.

The processes 300 and 400 may be used in conjunction with one another or separately in order to improve ECG circuits that may be susceptible to drive circuit saturation. For example, the artifact removal technique of process 400 may be used in conjunction with the process 300 in order to remove an unwanted artifact in an ECG output signal that is due to periodic current injections. Other minor variations and/or combinations of steps are within the scope of the present disclosure in order to adjust a current source to compensate for excess DC content that may build up on the drive circuit and lead to unwanted drive circuit saturation. Given the rise of low-voltage circuits that are susceptible to saturation given real-world ECG electrode impedances, this effect is desirable and helps to provide effective use of these lower-cost components in ECG systems.

The embodiments of the present disclosure may be implemented with any combination of hardware and software. In addition, the embodiments of the present disclosure may be included in an article of manufacture (e.g., one or more computer program products) having, for example, computer-readable, non-transitory media. The media has embodied therein, for instance, computer readable program code for providing and facilitating the mechanisms of the embodiments of the present disclosure. The article of manufacture can be included as part of a computer system or sold separately.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

Unless stated otherwise as apparent from the following discussion, it will be appreciated that terms such as "applying," "generating," "identifying," "determining," "processing," "computing," "selecting," or the like may refer to the actions and processes of a computer system, or similar electronic computing device, that manipulates and transforms data represented as physical (e.g., electronic) quantities within the computer system's registers and memories into other data similarly represented as physical quantities within the computer system memories or registers or other such information storage, transmission or display devices. Embodiments of the methods described herein may be implemented using computer software. If written in a programming language conforming to a recognized standard, sequences of instructions designed to implement the methods can be compiled for execution on a variety of hardware platforms and for interface to a variety of operating systems. In addition, embodiments of the present invention are not described with reference to any particular programming language. It will be appreciated that a variety of programming languages may be used to implement embodiments of the present invention.

In some embodiments, information associated with the ECG signal may be output to a graphical user interface (GUI). For example, in one embodiment, the GUI outputs the ECG signal itself as well as an indication of any current adjustments applied to address leakage issues. In some embodiments, a graphical alarm may be presented in the GUI to alert a physician to the presence of leakage. A "graphical user interface" (GUI), as used herein, comprises one or more display images, generated by a display processor and enabling user interaction with a processor or other device and associated data acquisition and processing functions. The GUI may also include an executable procedure or executable application that generates signals representing the GUI display images. These signals are supplied to a display device which displays the image for viewing by the physician (or other user). The processor, under control of an executable procedure or executable application, manipulates the GUI display images in response to signals received from the input devices. In this way, the user may interact with the display image using the input devices, enabling user interaction with the processor or other device.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters.

The functions and process steps herein may be performed automatically or wholly or partially in response to user command. An activity (including a step) performed automatically is performed in response to one or more executable instructions or device operation without user direct initiation of the activity.

The system and processes of the figures are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. As described herein, the various systems, subsystems, agents, managers and processes can be implemented using hardware components, software components, and/or combinations thereof. No claim element herein is to be construed under the provisions of 35 U.S.C. 112(f) the element is expressly recited using the phrase "means for."

I claim:

1. An Electrocardiography (ECG) system configured to produce an ECG output signal of a patient, the ECG system comprising:
   a plurality of electrodes forming a plurality of leads;
   a monitoring circuit configured to monitor a voltage differential on the plurality of leads and produce the ECG output signal based on the voltage differential;
   a drive circuit configured to cancel a common mode noise among the plurality of electrodes;
   a lead fault detection system comprising one or more current sources, each current source configured to produce a current to deliver to an associated electrode among the plurality of electrodes; and
   a control module configured to measure a parameter at each associated electrode, determine an amount of current leakage based on the measured parameter at each associated electrode, and perform periodic current injections via a current source at each associated electrode to compensate for the amount of the current leakage at each associated electrode, wherein an amplitude of each periodic current injection is determined based on the measured parameter.

2. The ECG system of claim 1, wherein each of the plurality of electrodes includes an associated current source among the one or more current sources in the lead fault detection system.

3. The ECG system of claim 2, wherein the control module is configured to adjust current injections from each current source based on the measured parameter of the associated electrode.

4. The ECG system of claim 1, wherein the measured parameter is one or more of a resistance, impedance, current or voltage at the associated electrode.

5. The ECG system of claim 1, wherein the measured parameter is indicative of a current leakage due to a contact state of one or more of the electrodes to the patient.

6. The ECG system of claim 1, wherein the one or more current sources produce direct current.

7. The ECG system of claim 6, wherein the control module is configured to pulse the direct current and create a pulsed voltage at each electrode.

8. The ECG system of claim 7, wherein the control module is configured to identify an artifact signal from the ECG output signal based on a time-amplitude correlation of the pulsed direct current and remove the artifact signal from the ECG output signal.

9. The ECG system of claim 1, wherein a rate of the periodic current injections is less than 0.05 Hz.

10. A method for avoiding oversaturation of a right leg drive circuit in an ECG system,
wherein the ECG system comprises:
a plurality of electrodes forming a plurality of leads;
a monitoring circuit
a drive circuit;
a lead fault detection system comprising one or more current sources; and
a control module;
the method comprising:
monitoring, with the monitoring circuit, a voltage differential on the plurality of leads and producing an ECG output signal based on the voltage differential;
cancelling, with the drive circuit, a common mode noise among the plurality of electrodes;
producing, with each of the one or more current sources, a current to deliver to an associated electrode among the plurality of electrodes;
measuring, with the control module, a parameter at each associated electrode;
determining, with the control module, an amount of current leakage based on the measured parameter at each associated electrode; and
performing, with the control module, periodic current injections via a current source at each associated electrode to compensate for the amount of the current leakage at each associated electrode, wherein an amplitude of each periodic current injection is determined based on the measured parameter.

11. The method of claim 10, wherein the parameter correspond to skin-electrode resistance at each electrode.

12. The method of claim 10, wherein the parameter correspond to skin-electrode impedance at each electrode.

13. The method of claim 10, wherein the parameter correspond to (a) skin-electrode resistance at each electrode and (b) skin-electrode impedance at each electrode.

14. The method of claim 10, wherein the parameter provide a measurement of bias currents flowing from the electrodes.

15. The method of claim 10, wherein the current source at each associated electrode produces direct current.

16. The method of claim 15, wherein the direct current produced by the current source at each associated electrode is pulsed by the control module.

17. The method of claim 16, further comprising:
identifying an expected signal based on a time-amplitude correlation of the pulsed direct current; and
remove an artifact from the ECG output signal that corresponds to the expected signal.

18. The method of claim 15, further comprising:
controlling the pulsing of the direct current to be less than a minimum high pass filter setting associated with the monitoring circuit of the ECG system.

* * * * *